(12) United States Patent
Daly et al.

(10) Patent No.: US 9,418,422 B2
(45) Date of Patent: Aug. 16, 2016

(54) SKIN IMAGE ANALYSIS

(71) Applicant: SKIN ANALYTICS LTD, London (GB)

(72) Inventors: Neil Daly, London (GB); Julian Hall, London (GB); Pietro Cavallo, London (GB)

(73) Assignee: SKIN ANALYTICS LTD (GB)

( * ) Notice: Subject to any disclaimer, the term of this patent is extended or adjusted under 35 U.S.C. 154(b) by 15 days.

(21) Appl. No.: 14/437,796

(22) PCT Filed: Nov. 7, 2013

(86) PCT No.: PCT/EP2013/073217
§ 371 (c)(1),
(2) Date: Apr. 22, 2015

(87) PCT Pub. No.: WO2014/072375
PCT Pub. Date: May 15, 2014

(65) Prior Publication Data
US 2015/0254851 A1    Sep. 10, 2015

(30) Foreign Application Priority Data

Nov. 9, 2012   (EP) .................................... 12192126

(51) Int. Cl.
| | | |
|---|---|---|
| G06K 9/00 | (2006.01) | |
| G06T 7/00 | (2006.01) | |
| A61B 5/00 | (2006.01) | |
| G06T 5/00 | (2006.01) | |

(52) U.S. Cl.
CPC ............... *G06T 7/0014* (2013.01); *A61B 5/444* (2013.01); *G06T 5/002* (2013.01); *G06T 5/003* (2013.01); *G06T 7/0016* (2013.01); *G06T 2207/10004* (2013.01); *G06T 2207/20081* (2013.01); *G06T 2207/30088* (2013.01); *G06T 2210/32* (2013.01); *G06T 2210/41* (2013.01)

(58) Field of Classification Search
None
See application file for complete search history.

(56) References Cited

U.S. PATENT DOCUMENTS

| | | | | |
|---|---|---|---|---|
| 6,067,369 | A  * | 5/2000 | Kamei ................. | G06K 9/4633 |
| | | | | 382/125 |
| 8,027,521 | B1 * | 9/2011 | Moon ................. | G06K 9/00288 |
| | | | | 382/118 |
| 9,189,886 | B2 * | 11/2015 | Black ................. | G06K 9/00369 |
| 2009/0326383 | A1 * | 12/2009 | Barnes ................. | A61B 5/0059 |
| | | | | 600/476 |
| 2011/0040192 | A1 | 2/2011 | Brenner et al. | |
| 2012/0010513 | A1 * | 1/2012 | Wong ................. | A61B 1/00165 |
| | | | | 600/476 |

OTHER PUBLICATIONS

International Search Report for PCT/EP2013/073217 dated Jan. 23, 2014, 4 pages.
Konstantin, Korotkov et al., "Computerized analysis of pigmented skin lesions: A review," Artificial Intelligence in Medicine, vol. 56, 69-90, Elsevier B.V., 2012.
Tan, Xiaoyang et al., "Face Recognition from a Single Image per Person: A Survey," Pattern Recognition, vol. 39, 1725-1745, Elsevier B.V., Sep. 2006.
Wadhawan, Tarun et al., "SkinScan(c): A portable library for melanoma detection on handheld devices," Proc IEEE Int Symp Biomed Imaging, 133-136, Mar. 30, 2011.

* cited by examiner

*Primary Examiner* — Shervin Nakhjavan
(74) *Attorney, Agent, or Firm* — Hovey Williams LLP

(57) ABSTRACT

Method of processing an image of the skin is disclosed. The method comprises the receipt of skin image data, the generation of simulated images with artificial transformation and the analysis of the simulated images to form a vector from extracted features.

19 Claims, 3 Drawing Sheets ated application under 35 U.S.C. 371 of International Application No. PCT/EP2013/073217, filed Nov. 7, 2013, which is incorporated by reference herein in its entirety.

SKIN IMAGE ANALYSIS

RELATED APPLICATION

The present application is a national stage application under 35 U.S.C. 371 of International Application No. PCT/EP2013/073217, filed Nov. 7, 2013, which is incorporated by reference herein in its entirety.

The present invention relates to a method and system for receiving and analysing images of human skin. The skin is the human body's largest organ and one that evolves and changes over time. These changes can be used as an indicator of disease, as well as both an indicator and proxy for good health and perceptions of beauty, so there is a need to provide a method and system for analysing such changes over time.

Skin conditions that would benefit from monitoring include the following.

Wound monitoring, monitoring of the morphology, colour and texture of the skin over time, with a view to tracking the rate of wound healing, with or without the application of a topical treatment.

Beauty product effectiveness, monitoring the change in the morphology, colour and texture of the skin over time, including skin tone, blemishes and wrinkles, with a view to tracking the effectiveness of topical treatments applied to the skin, such as anti-aging creams.

Diabetes is often associated with skin conditions such as diabetic dermopathy, diabetic bullae and diabetic stiff skin. Monitoring these conditions will assist in the evaluation of the efficacy for treatment of diabetes.

Monitoring change in the texture, morphology and colour of skin prone to acne, with a view to tracking the effectiveness of topical treatments applied to the skin.

Skin cancer monitoring, with the tracking of the evolution of skin lesions over time, with a view to the early detection of melanoma.

Sun exposure risk evaluation in which the colour of the skin and relative changes in colour can be used to provide a risk profile for selected conditions.

Whilst some methods of tracking the evolution of skin over time exist, such methods and the systems employing them usually require expensive imaging equipment in order to ensure consistency of image, and often rely on a manual review of the images. This means that an individual has to make inconvenient visits to the location of the equipment, making monitoring of change over time inconvenient and time consuming, limiting widespread monitoring of changes over a large number of individuals.

No convenient, measurable and accessible solution exists for the general population to accurately track their skin over time using any image they provide, whether that be from a smartphone, camera or other image capturing device, either using single or video images.

This is because currently there is no technology capable of overcoming the differences in a temporal sequence of images of the skin that would result from the differences, such as lighting conditions, focal lengths and camera angles, caused by the different conditions under which a time series of such images could be captured.

The present invention seeks to provide a system and method for analysing images of the skin generated during the above-mentioned or similar types of monitoring regimes, and generated from low cost imaging device by untrained users, to provide data indicative of significant changes in the skin morphology.

According to the present invention there is provided a method of processing an image of the skin, the method comprising the steps of: receiving skin image data; generating a set of simulated images, each artificially transformed by a different noise generating parameter; analysing each of the simulated images to extract one or more skin feature to be monitored; forming a vector from each extracted feature such that every simulated image is represented by a related vector; creating a distribution within a hyperspace from the vectors; and determining from the distribution the location of data relating to the at least one feature within the hyperspace.

The method may further comprise the steps of receiving second image data relating to the same skin but obtained at a different time; generating a second distribution by following the steps above; and comparing the first and second distributions to provide change data to a user to determine any change in the at least one feature to be monitored.

The method may monitor plural skin features and in this case may further comprise the steps of: operating a machine learning algorithm employed to assign a weight to each feature and/or a combination of features, in order to identify which features or combination of features set is most relevant for identifying change in skin images.

If a skin feature being monitored has an area associated with it and a change in that area is to be monitored then the method may further employ a spatial map and the steps of analysing data relating to the structure of the skin around the area to produce area reference data, and using the reference data in conjunction with our approach described below to remove noise, to normalise the image by aligning the structure data in the two related images.

A system for performing the method defined above is also provided and comprises means for receiving image data from an image retrieval device, a processing component for processing the image data in accordance with the above method, and means for forwarding the data for review by a user. The system may further comprise a display for displaying processed data and may be configured to receive image data from a source remote from the processing component.

The present invention provides an inexpensive and convenient method and system which can enable the general population to track changes in their skin and be alerted to any relevant changes. With skin cancer, it can enable a method of providing additional visual information on the evolution of a skin lesion at the time a patient presents to a medical professional whereas current diagnosis is mostly conducted on the lesion 'as is' at the time of presentation and does not cover the historic evolution of the lesion. It also enables an in-clinical application, to assist in the improved detection of changes in lesions by either supporting or automating the work of in-clinic experts who currently review skin lesion evolution manually.

Examples of the present invention will now be described with reference to the accompanying drawings, in which.

Examples of the present invention will be described with reference to a monitoring regime for the early detection of skin cancer. It will be appreciated however that the same methods and systems can be used for monitoring for other types of skin change of the types listed above, for example. Early detection of skin cancer is well known to be highly beneficial in improving the prognosis for treatment. The deadliest form of skin cancer, malignant melanoma, is characterised by change in pigmented skin lesions; research suggests that change in a lesion is the most sensitive indicator of melanoma. Of course, there can be benign changes in lesions also and it is useful also to identify which changes are benign to improve the accuracy of analysis. To monitor this change, skin screening clinics have been used to photograph images of patients over time. However this solution is by its very nature expensive, requires a visit to the clinic and is reliant solely on the manual review of the patient's images. Alternatively, technology for analysing the perceived risk of a skin lesion, at a static point time, does exist (for example, through the use of fractal analysis or machine learning techniques used to classify images into benign and malignant lesions), but none of these techniques are currently capable of identifying discreet change in the presence of variations in the conditions under which an image has been taken.

Figure 1:
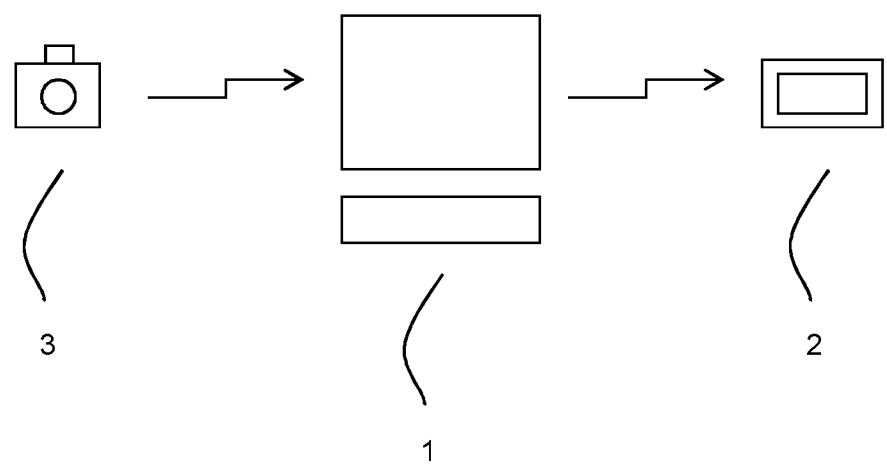
FIG. 1 is a schematic diagram showing the main components of a system employing the method of the present invention.

Referring to FIG. 1, a system employing the present invention has a central processing component 1 which can be provided an appropriately adapted PC for example. This processing component is connected either directly or remotely to a display device 2 which provides the results of processing to an end user, such as a medical practitioner.

Also connected to the processing component, again either remotely or directly is an image capture device 3. This may be a device 3 provided solely for use with the system, or may be a subject's own device, such as a web cam, mobile telephone camera or similar, or could be a dermascope. The device 3 may have dedicated software on is to aid communication with the processing component 1 or may simply communicate with that component 1 through a conventional communication medium such as the internet.

It may be that, for certain applications, the imaging device also acts as the display device 2 to provide the output of the analysis by the processing component 1 to a user. With the system a user may be able to select the destination of processed data sent from the processing component 1 so that the user's doctor, for example, can be selected as a recipient for review of the data.

The system is operated by a user capturing an image of the region of skin to be monitored with the image capture device 3 and forwarding it to the processing component 1. The image may be a single image, a sequence of images or video.

The received image data is processed using the approach described below. If it is an initial image then the processing generates reference data in accordance with the approach for subsequent comparison with later image data. If the image data is to be related to image data obtained previously then it too is processed in accordance with the approach below and compared with the earlier processed data. An output is provided by the processing component based on the processing for use in monitoring the condition of interest.

In any time series images of the skin, captured under non-controlled conditions, there will be differences caused by features such as lighting conditions, focal lengths, camera perspective, the rotation of the image, the relative position of the captured image area, blurring, and camera resolution.

These differences create noise between the images that interferes with the detection of any morphological change in the skin lesion itself. Current approaches to this problem would be to normalise the images, i.e. mathematically transforming the second image to the identical conditions of the first image. However, this approach to the problem of tracking lesions does not work without one or more fixed and static reference points, such as permanent markers of fixed and known size, position and colour on the skin, that can be used to baseline the image and determine which changes are due to the noise, and which are due to an actual change in the skin lesion itself. As this is not generally possible in the case of skin due to natural variations in skin such as weight gain, stretch or the introduction of wrinkles, the efficacy of such a system is difficult to apply in practice.

To solve this problem, the present invention provides a method of removing the noise between temporal images to a sensitivity at which actual changes in the skin can be detected with adequate reliability.

When describing the invention it is useful to outline some terminology. In the description, a feature of the image is a measurement of a characteristic component of either the image or part of the image. A signal is the change in the measurement of a feature over time. Noise is the component part of the signal which is attributable to changes in the conditions under which the image was taken with respect to other images, and not attributable to the actual physical change being tracked. A detected change is that part of the signal which is attributable to physical change in the skin lesion only, and not attributable to any noise.

Using the skin cancer monitoring example, the defining and operation of a system according to the invention needs certain preliminary identifiers to be determined. In this example we have firstly determined which features of skin lesions are least sensitive to the noise. By themselves, no one individual feature is robust enough to differentiate which part of a signal is down to actual physical change in the lesion and which is attributable to noise. Therefore the first step in creating the algorithm is to identify not only features that are least sensitive to noise, but additionally, which combination of these features are least sensitive to noise. Furthermore, in order to be able to classify the nature of the change of the skin lesion (in this case, into measures of change classified by Asymmetry, Border and Colour), it is beneficial to also classify the combination of features into the measures which they best relate. Once this classification is established the parameters of the processing method used by the processing component 2 can be set.

The next step in being able to detect change, in the absence of any known absolute fixed and static reference points that allow transformation, is to separate the noise and detected change components of the constituent signals that are most robust to noise. We will illustrate how this is carried out using the example of differing perspectives between images.

In order to make the method robust to perspective, in other words, to artificially remove the impact of noise, we simulate a broad range of possible perspectives, applying numerous geometric perspective transformations to an image. This means for each user captured image, the processing component 2 generates a large set of simulated images, each artificially transformed to a different perspective. Each of these images is then analysed and the N features (directly or indirectly related to the standard classification of lesions in skin cancer analysis) will be extracted. These extracted features will form a vector. Hence, every artificial image will be represented by its N-dimension feature vector.

This means that an artificial image can be thought as a point in a N-dimension hyperspace.

All the artificial images associated to the original image are then used to create a distribution. From that, we know which part of the hyperspace is associated to the base skin lesion. Once this data is compared to a later image, if a changed lesion is present in the later image and different in one or more features we expect it to lie outside of the distribution built before or, to be more precise, we expect the distance between the two distributions to be higher than a certain threshold. In fact, the second lesion can be extremely distorted in terms of perspective and can lie inside the first distribution, but if we generate a second distribution we will notice that this is distant enough from the first one, thereby identifying it is a changed lesion.

So the system builds a distribution for each lesion and observes how distant are these distributions from each other. For example the system measures the distance from a fixed reference point (such as the first centroid) and each centroid and then plotting that distance. The distance between centroids can be measured using any distance metric including, but not limited, Euclidean distance and Mahalanobis distance.

Figure 2:
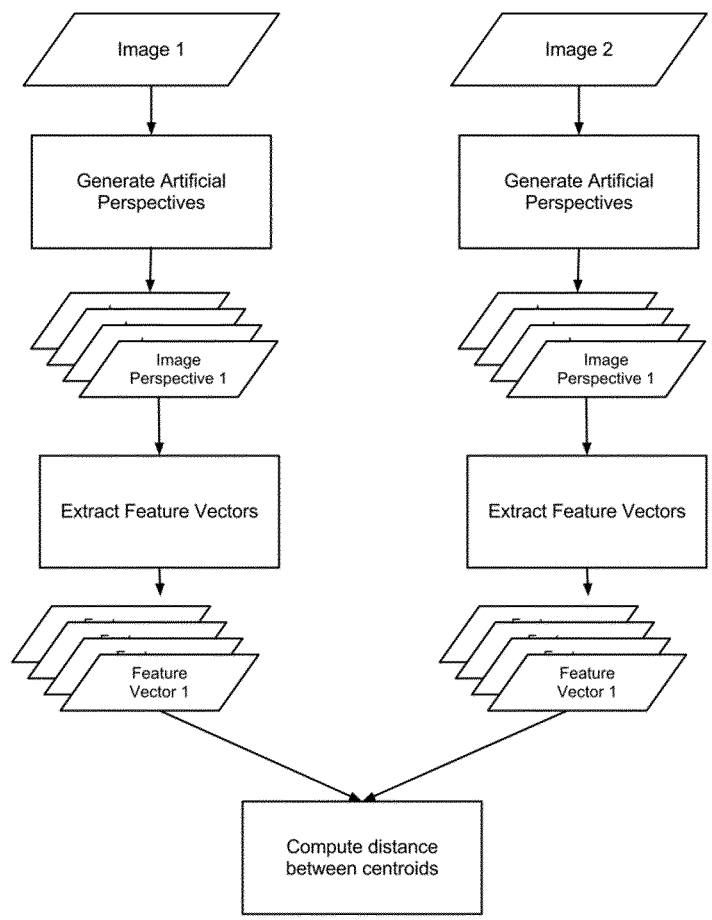
FIG. 2 is a flow diagram showing the main steps in a method according to the present invention.
Figure 3:
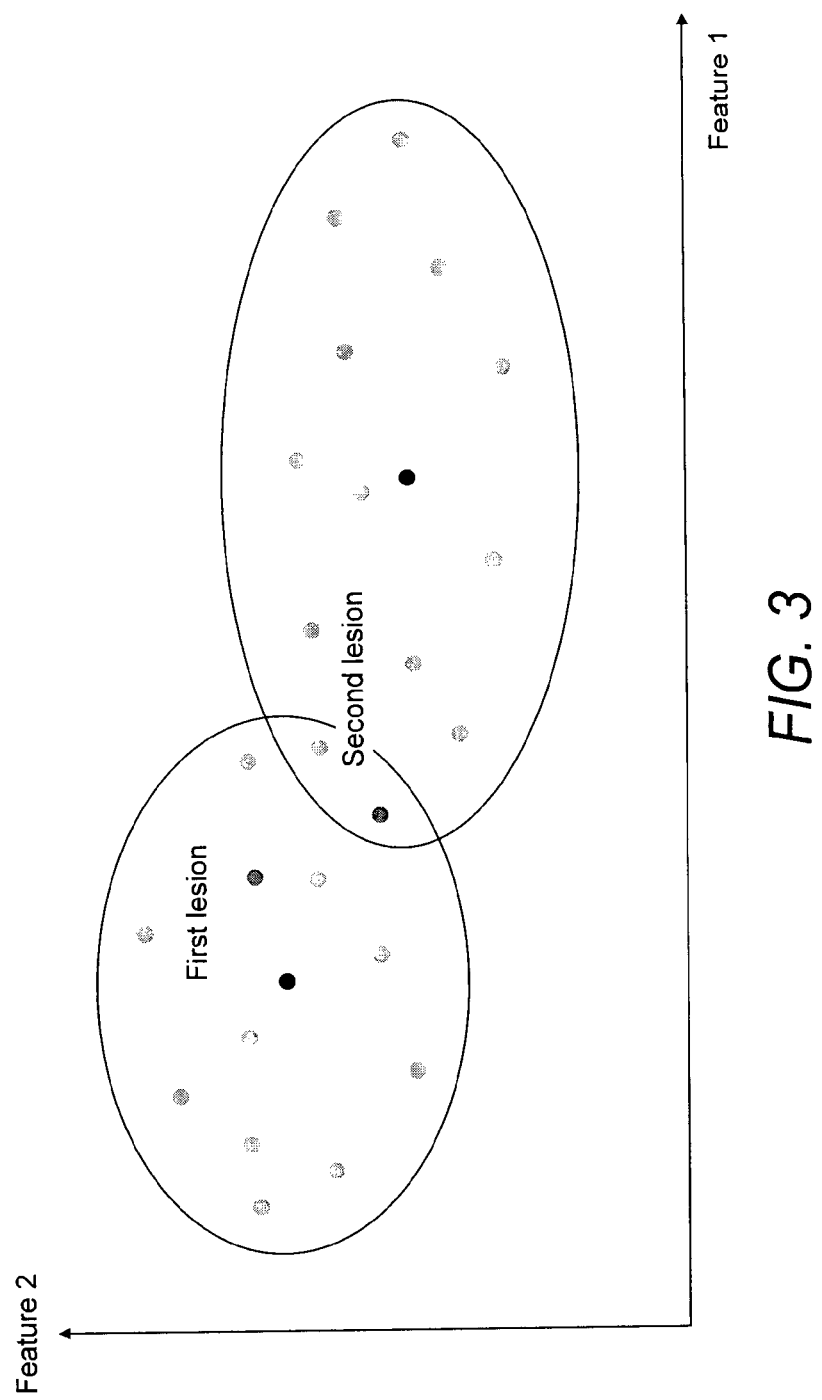
FIG. 3 is a diagram showing part of the analysis technique of the method of the invention.

For the purpose of illustration we have represented this method in FIG. 2 in a simplified, two-dimensional form.

The same principle can be applied to any of the variances we might expect between images. In the case of illumination this would involve generating artificial images with different illumination, and applying exactly the same process outlined above. Of course, different types of image capture device may provide additional image data that can aid in noise removal. For example a depth sensing or 3D camera may provide additional information that can assist in the generation of simulated images and improved noise removal.

When creating the method, parameters for the processing component 2 can be calculated under controlled conditions for a series of images to ascertain the distance between distributions that will represent actual detected change, as opposed to noise, and this information used to finalise the parameters of the method that will be used by the system.

Additionally by classifying the changed parameters against a large number features, we build a personalised distribution of 'normal' changes for each unique user. In this model, we could identify changes that are uncharacteristic for that user. Furthermore, by extending this classification, we can build a population-wide model of features that are uncharacteristic of normal change.

By way of example, using the above technique to create an analysis method for images for monitoring skin cancer, the following features have been determined to be least sensitive to noise. We have classified them by the measurement to which they best relate. Many features have been evaluated in order to describe a skin lesion and to detect change. They can be divided into Asymmetry, Borders and Colour/Texture related features. By themselves, some of these features are more robust than others (leading to tighter or more dispersed distributions respectively), hence the importance of the multi-dimensional technique used to eliminate noise.

Asymmetry descriptors that have been evaluated include, but are not limited, to:
  Circularity Ratio and Bulkiness, which are used to describe the relative circularity or ellipticalality of the skin lesion.
  Convex Ratio and Concavity tree to describe the relative convexity of the shape of the lesion,
  Asymmetry on both axes.

Border descriptors that have been evaluated include, but are not limited, to
  Hu invariant moments, which are used to consistently describe the shape of the skin lesion under conditions of perspective, rotation and distance changes.
  Fractal dimension, which is used to describe how 'fractal' the borders are.
  Gradient magnitude of border and body of the lesion and their uniformity to describe the roughness of the edges and of the internal structure.
  SD measure to measure the roughness of the border.
  Signature analysis, whereby a signature is traced following the borders and considers the radius from the centre of mass and the pixel on the border.

The following methods were applied to analyse the signals: Fourier Coefficients, Complex Wavelet Coefficients, Central Moments and Parameters of an Autoregressive Model. Those methods are used to represent the shape of the signal as well as the frequency spectrum.

Colour/Texture descriptors that have been evaluated include, but are not limited, to:
  Uniformity on each colour layer in different colour spaces (for example. RGB, HSV).
  Standard Deviation on each colour layer.
  Colour segmentation and study of the size and shape of the different colour areas.
  Global Entropy on the grey scale image.
  Different measures based on the Gary Co-occurrence Matrix: Contrast, Correlation, Energy, Homogeneity.
  Haralick features.

There are further techniques that can be used in conjunction with the above approach to yet further improve the accuracy of the change detection.

For example, to assess diameter a spatial map can be used. This includes an analysis of the structure of the skin around the lesion, and use of that data to normalise the image by aligning the structures in the two images (registration). In this case, the distance between distributions approach needs be employed to ensure the validity of this technique.

In addition or instead of this a machine learning algorithm can be employed to assign a weight to each feature and combination of features, in order to understand which feature set is most relevant for identifying change. Furthermore, in the case of image analysis for skin cancer such machine learning algorithms can also help to discriminate between a malignant and a benign change according to which feature set has changed and by how much.

The system may also enable the provision of feedback data to be provided to the processing component 1. This data may be provided by the user or an expert such as a medical professional or may have been generated automatically from the analysis of images from other users. This feedback data can be used to improve both noise removal and the selection and weighting of the relevance of features to be monitored so that the system can be adaptive and its accuracy improve over time.

The invention claimed is:

1. A method of processing an image of the skin, the method comprising the steps of:
  receiving skin image data;
  generating a set of simulated images, each artificial transformed by a different noise generating parameter;
  analysing each of the simulated images to extract one or more skin feature to be monitored;
  forming a vector from each extracted feature such that every simulated image is represented by a related vector;
  creating a distribution within a hyperspace from the vectors; and
  determining from the distribution the location of data relating to the at least one feature within the hyperspace.

2. The method of claim 1, further comprising the steps of:
  receiving second image data relating to the same skin but obtained at a different time;
  generating a second distribution by generating a second set of simulated images, each artificially transformed by a different noise generating parameter;
  analysing each of the second set of simulated images to extract one or more skin feature to be monitored;

forming a vector for from each extracted feature such that every simulated image is represented by a related vector; creating a distribution within a hyperspace from the vectors; and determining from the second distribution the location of data relating to the at least one feature within the hyperspace; and comparing the first and second distributions to provide change data to a user to determine any change in the at least one feature to be monitored.

3. The method of claim 1, further comprising the steps of employing an introduced reference point and generating the distribution from the transformed images based on the reference point to provide a further noise reduction.

4. The method of claim 1 in which plural skin features are monitored and further comprising the step of operating a machine learning algorithm employed to assign a weight to each feature and/or a combination of features, in order to identify which features or combination of features set is most relevant for identifying change in skin images.

5. The method of claim 1, in which a skin feature being monitored has an area associated with it and a change in that area is monitored, the method further comprises the step of generating a spatial map and die steps of analysing data relating to the structure of the skin around the area to produce area reference data, and using the reference data in conjunction with the distance between distribution analysis to normalise the image by aligning the structure data in the two related images.

6. The method according to claim 1, wherein the one or more features to be monitored are indicators of skin cancer.

7. The A method according to claim 1, wherein the noise generating parameter is at least one of perspective, captured image area, blurring, camera resolution, distance, focal distance, rotation, skin tone, skin stretching or illumination level and origin.

8. A system for performing the method of claim 1 and comprising:
means for receiving image data from an image retrieval device,
a processing component for processing the image data in accordance with the method, and
means for forwarding the processed data for review by a user.

9. The system of claim 8, further comprising a display for displaying the processed data.

10. The system of claim 8, wherein the means for receiving image data is remote from the processing component.

11. A method of processing an image of the skin, the method comprising the steps of:
receiving skin image data;
generating a set of simulated images, each artificially transformed by a different noise generating parameter;
analysing each of the simulated images to extract one or more skin feature to be monitored;
forming a vector from each extracted feature such that every simulated image is represented by a related vector; creating a distribution within a hyperspace from the vectors; and
determining from the distribution the location of data relating to the at least one feature within the hyperspace;
receiving second image data relating to the same skin but obtained at a different time;
generating a second distribution by generating a second set of simulated images, each artificially transformed by a different noise generating parameter;
analysing each of the second set of simulated images to extract one or more skin feature to be monitored;
forming a vector for from each extracted feature such that every simulated image is represented by a related vector; creating a distribution within a hyperspace from the vectors; and
determining from the second distribution the location of data relating to the at least one feature within the hyperspace; and comparing the first and second distributions to provide change data to a user to determine any change in the at least one feature to be monitored; and
operating a machine learning algorithm employed to assign a weight to each feature and/or a combination of features, in order to identify which features or combination of features set is most relevant for identifying change in skin images.

12. The method of claim 11, further comprising the steps of employing an introduced reference point and generating the distribution from the transformed images based on the reference point to provide a further noise reduction.

13. The method of claim 12 in which plural skin features are monitored and further comprising the step of operating a machine learning algorithm employed to assign a weight to each feature and/or a combination of features, in order to identify which features or combination of features set is most relevant for identifying change in skin images.

14. The method of claim 13, in which a skin feature being monitored has an area associated with it and a change in that area is monitored, the method further comprises the step of generating a spatial map and the steps of analysing data relating to the structure of the skin around the area to produce area reference data, and using the reference data in conjunction with the distance between distribution analysis to normalise the image by aligning the structure data in the two related images.

15. The method according to claim 14, wherein the one or more features to be monitored are indicators of skin cancer.

16. The method according to claim 11, wherein the noise generating parameter is at least one of perspective, captured image area, blurring, camera resolution, distance, focal distance, rotation, skin tone, skin stretching or illumination level and origin.

17. The method of claim 11 in which plural skin features are monitored and further comprising the step of operating a machine learning algorithm employed to assign a weight to each feature and/or a combination of features, in order to identify which features or combination of features set is most relevant for identifying change in skin images.

18. The method of claim 11, in which a skin feature being monitored has an area associated with it and a change in that area is monitored, the method further comprises the step of generating a spatial map and the steps of analysing data relating to the structure of the skin around the area to produce area reference data, and using the reference data in conjunction with the distance between distribution analysis to normalise the image by aligning the structure data in the two related images.

19. The method according to claim 11, wherein the one or more features to be monitored are indicators of skin cancer.

* * * * *